United States Patent [19]

Weinberger

[11] Patent Number: Plant 5,473

[45] Date of Patent: May 21, 1985

[54] NECTARINE TREE, SUNECTTWELVE

[75] Inventor: John H. Weinberger, Fresno, Calif.

[73] Assignee: Superior Farming Company, Bakersfield, Calif.

[21] Appl. No.: 555,190

[22] Filed: Nov. 25, 1983

[51] Int. Cl.[3] ..... A01H 5/00

[52] U.S. Cl. ..... Plt./41

[58] Field of Search ..... Plt./41

*Primary Examiner*—James R. Feyrer

*Attorney, Agent, or Firm*—Huebner & Worrel

[57] ABSTRACT

A new and distinct variety of nectarine tree generally similar to the Fantasia (unpatented) which it most nearly resembles but from which it is distinguished by producing fruit having a more extensive red skin color, fewer cleft sutures, a rounder shape and brighter ground color.

1 Drawing Figure

BACKGROUND OF THE NEW VARIETY

The present invention relates to a new and distinct variety of nectarine tree which is generally similar to the Fantasia Nectarine Tree (unpatented), which it most nearly resembles, but which bears fruit having a more substantial amount of red skin coloration, fewer cleft sutures, a rounder shape, and a brighter ground color than that of the Fantasia.

The Fantasia variety of nectarine tree is well known in the industry as a productive bearer of freestone fruit having a bright yellow ground color covered over one-third to two-thirds of its skin surface by a bright red blush. However, despite the success of the Fantasia variety, it is disadvantageous in that the coloring of the skin of the fruit is uneven, and this deficiency is one of the more important factors taken into account by consumers when selecting among varieties in the marketplace. Further, the Fantasia variety suffers the further deficiency of, in some years, bearing fruit having a distinctly pointed apex. Such variability of shape places the Fantasia at a marked disadvantage in commercial competition against varieties ripening at roughly the same time and having a more uniformly round shape.

Thus, it has long been recognized that it would be highly desirable to provide a nectarine tree which bears fruit having a consistently round shape and a highly and evenly colored red skin. Further, it has been known that it would be desirable to have such a nectarine tree whose fruit is of a smoother exterior surface texture, and which exhibits fewer cleft sutures than that of the Fantasia.

ORIGIN AND ASEXUAL REPRODUCTION OF THE NEW VARIETY

The new variety of nectarine tree was discovered by me in 1978 growing as an open pollinated seedling of a Fantasia Nectarine Tree in an orchard owned by Superior Farming Company of Bakersfield, Calif. and located at 5090 East Church Ave., Fresno, Calif. The variety originated in a planned breeding program conducted by me on the aforementioned property. The seedling was grown to fruiting and was selected by me for propagation at that location.

The new variety was asexually reproduced by budding, that is by inserting buds from the variety into other trees or rootstocks. The buds were forced into growth and eventually produced fruit. Such asexual reproduction was carried out by me and by my assistants under my direction and supervision. The fruit and tree characteristics resulting from this propagation proved identical to those of the original seedling.

SUMMARY OF THE NEW VARIETY

The instant variety of nectarine tree is broadly characterized by perpetuating the general characteristics of the Fantasia Nectarine Tree (unpatented) in the ripening of its fruit and the fruit's general appearance, but is distinguished therefrom as to novelty by the appreciably greater amount of external red skin coloring, the lesser amount of cleft sutures, brighter ground color, by the more globular shape of the fruit, particularly in that the apex is not pointed.

The new nectarine tree bears fruit whose flesh is yellow with a reddish tinge, ripening evenly and having a good eating quality. The flesh is completely freestone, the stone parting from the flesh smoothly. The skin of the fruit has a substantially even coloration, with an attractive red blush color (Plate 40-14) on a bright yellow ground color (Plate 29-6).

BRIEF DESCRIPTION OF THE DRAWING

The accompanying drawing is a color photograph of three mature nectarines of the subject variety, one of which has been divided to show the flesh and stone characteristics, together with a representative twig bearing characteristic leaves.

DETAILED DESCRIPTION

Referring more specifically to the pomological details of the new and distanct variety of nectarine tree, the following has been observed under the ecological conditions prevailing in the designated orchard in Fresno County, Calif. All color code plate identifications, other than conventional color terminology, are by reference to the Munsell Limit Color Cascade.

TREE

Size: Medium. Depending on pruning practices.

Figure: Upright; spreading dense; round-topped. Controlled by pruning.

Vigor: Medium.

Productivity: Productive.

Regularity of bearing: Regular.

Trunk:

*Diameter in relation to length.*—Medium.

*Surface characteristics.*—Medium.

Branches:

*Size.*—Medium.

*Surface character.*—Medium.

*Color.*—Brown, dull.

*Lenticels.*—Number — medium; size — medium.

Leaves:

*Size.*—Medium.

*Length.*—150 mm.

*Width.*—38 mm.

*Shape.*—Ovate, lanceolate, acutely pointed.

*Thickness.*—Medium.

*Color.*—Medium green.

*Texture.*—Smooth.

*Marginal form.*—Crenate.

*Petiole.*—Length — medium; thickness — medium.

*Stem glands.*—Average number — two; arrangement — irregular, opposite; size — medium; type — reniform; position — on petiole and blade, at base of blade; stipules — dehisced.

Flower buds:

*Size.*—Medium.

*Length.*—Medium.

*Shape.*—Plump.

*Surface.*—Appressed, pubescent.

Flowers:

*Date of full bloom.*—March 11 in 1982; medium compared with other varieties.

*Size.*—Large.

*Color.*—Pink.

FRUIT

Maturity: Firm ripe July 30 (in 1982).

Size: Uniform, medium.

*Axial diameter.*—75 mm.

*Diameter transverse in suture plane.*—75 mm.

*Diameter transverse at right angle to suture plane-*.—69 mm.

Form:

*Symmetry.*—Uniform, broadly globose.

*Suture.*—Distinct, shallow line, extending from base but discontinuous at apex; slight depression beyond pistil point.

*Ventral surface.*—Rounded slightly, lipped throughout; lips unequal but variable.

*Stem cavity.*—Fairly abrupt, elongated in suture plane with suture showing on one side; depth — 11 mm.; breadth — 21 mm.

*Base.*—Rounded.

*Apex.*—Short, rounded.

*Pitsil point.*— *Apical.*

*Stem.*—Length — medium; caliper — medium.

Skin:

*Thickness.*—Medium.

*Texture.*—Medium, tenacious to flesh.

*Tendency to crack.*—None in dry season.

*Down.*—Wanting.

*Ground color.*—Plate 29-6.

*Blush color.*—Plate 40-14.

Flesh:

*Color.*—Yellow (Plate 29-9) with reddish tinge, mottled with red next to stone.

*Surface of pit cavity.*—Plate 35-13.

*Amygdalin.*—Wanting.

*Juice.*—Moderate.

*Texture.*—Firm, fine, melting.

*Fibers.*—Few.

*Ripening.*—Even.

*Flavor.*—Acid, delicate.

*Aroma.*—Faint.

*Eating Quality.*—Good.

Stone: Free, parts from flesh smoothly.

*Fibers.*—Short.

*Size.*—Large to medium; length — 41 mm.; breadth — 28 mm.; thickness — 21 mm.

*Form.*—Obovoid.

*Base.*—Slightly oblique.

*Hilum.*—Broad oval.

*Apex.*—Rounded.

*Sides.*—Equal.

*Surface.*—Regularly furrowed toward apex; ridged toward apex; pitted from base to above center.

*Ridges.*—Rounded, continuous.

*Pits.*—Elongated.

*Ventral edge.*—Thin with wing toward apex.

*Dorsal edge.*—Full, with deep, narrow groove to above center.

*Color.*—Plate 35-14.

*Tendency to split.*—Slight.

Use: Market.

Keeping quality: Good.

Resistance to disease: Medium.

Shipping quality: Good.

Although the new variety of nectarine tree possesses the described characteristics as a result of the growing conditions in Fresno County, California, in the central part of the San Joaquin Valley, it is to be understood that variations of the usual magnitude in characteristics incident to growing conditions, fertilization, pruning and pest control are to be expected.

Having thus described and illustrated my new variety of nectarine tree, what I claim as new and desire to secure by Letters Patent is:

1. A new and distinct variety of nectarine tree, substantially as illustrated and described, broadly characterized by its general resemblance to the Fantasia Nectarine Tree (unpatented), of which it is a seedling, but from which it is distinguished as to novelty by its fruit having a substantially greater amount of overall red blush on a brighter yellow ground color, fewer cleft sutures, and a rounder shape of fruit, particularly the apex thereof.

* * * * *

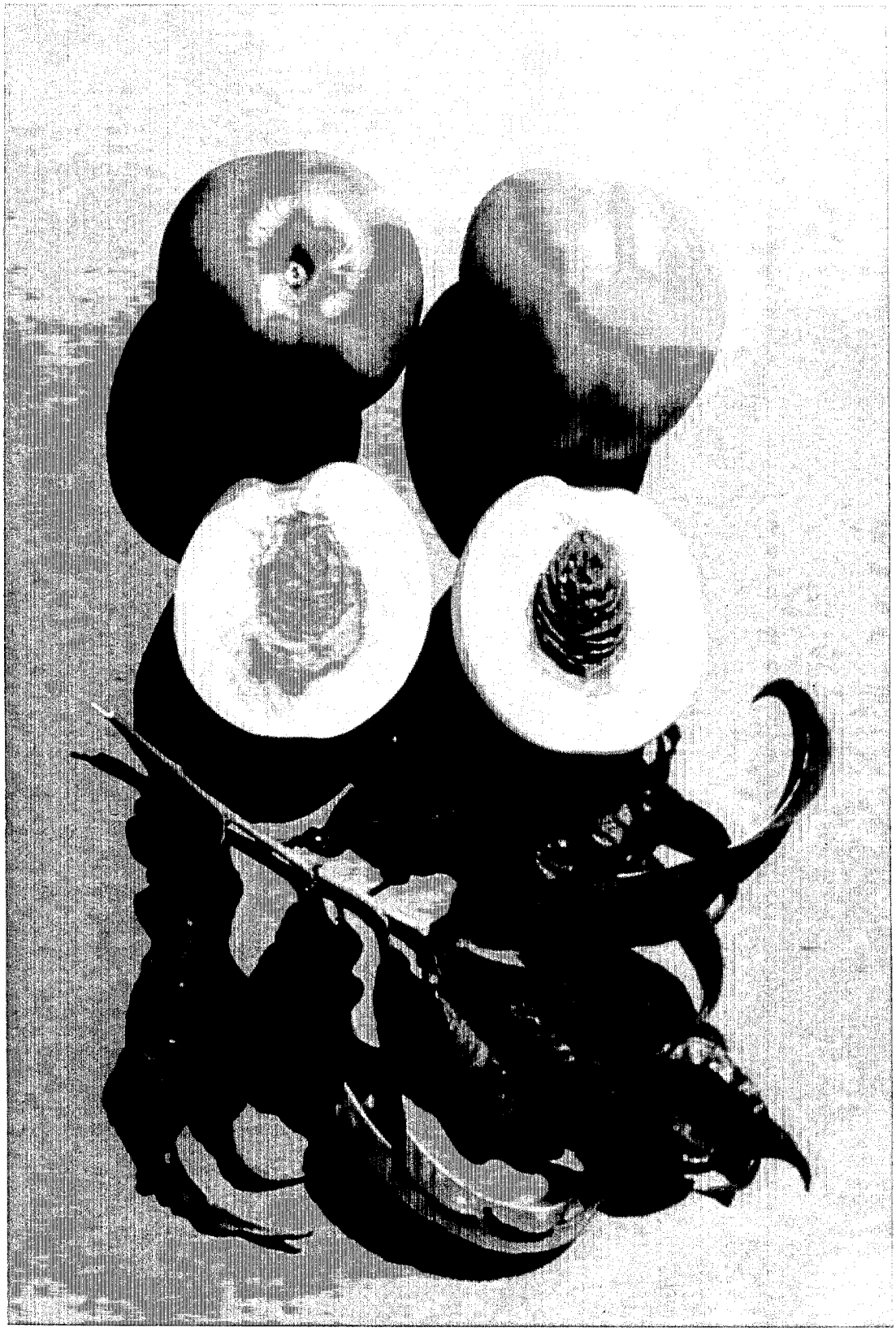

UNITED STATES PATENT AND TRADEMARK OFFICE

CERTIFICATE OF CORRECTION

PATENT NO. : PP 5,473

DATED : May 21, 1985

INVENTOR(S) : John H. Weinberger

It is certified that error appears in the above-identified patent and that said Letters Patent is hereby corrected as shown below:

Column 2, line 32, delete "distanct" and insert

---distinct---.

Column 2, line 42, "spreading" should read --spreading;--.

Signed and Sealed this

*Seventeenth* Day of *December 1985*

[SEAL]

*Attest:*

DONALD J. QUIGG

*Attesting Officer*

*Commissioner of Patents and Trademarks*